(12) United States Patent
Tanahashi

(10) Patent No.: US 10,039,437 B2
(45) Date of Patent: Aug. 7, 2018

(54) IMAGE PICKUP APPARATUS FOR ENDOSCOPE

(71) Applicant: OLYMPUS CORPORATION, Tokyo (JP)

(72) Inventor: Fuminori Tanahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/493,902

(22) Filed: Apr. 21, 2017

(65) Prior Publication Data
US 2017/0224203 A1 Aug. 10, 2017

Related U.S. Application Data

(63) Continuation of application No. PCT/JP2015/078085, filed on Oct. 2, 2015.

(30) Foreign Application Priority Data

Mar. 10, 2015 (JP) ................................. 2015-047445

(51) Int. Cl.
*H04N 5/225* (2006.01)
*H05K 3/36* (2006.01)
(Continued)

(52) U.S. Cl.
CPC ................ *A61B 1/04* (2013.01); *A61B 1/005* (2013.01); *A61B 1/00045* (2013.01);
(Continued)

(58) Field of Classification Search
CPC ...... H04N 5/2252; H05K 3/366; H05K 1/111; H05K 1/144
See application file for complete search history.

(56) References Cited

U.S. PATENT DOCUMENTS 7,571,540 B2 * 8/2009 Aonuma .................. H05K 3/44
174/250
8,295,014 B1 * 10/2012 Teo ........................ G11B 5/486
360/245.9
(Continued)

FOREIGN PATENT DOCUMENTS

JP   H04-253392 A   9/1992
JP   2003-031915 A   1/2003
(Continued)

OTHER PUBLICATIONS

International Search Report dated Dec. 8, 2015 issued in PCT/JP2015/078085.
(Continued)

*Primary Examiner* — Nathan Milakovich
(74) *Attorney, Agent, or Firm* — Scully, Scott, Murphy & Presser, P.C.

(57) ABSTRACT

An image pickup apparatus for an endoscope of the present invention includes a first circuit board on which a lead portion, a window portion in which a part of the lead portion is exposed, and a second circuit board on which a circuit pattern is fixed by soldering to the lead portion exposed on the window portion, and the lead portion that is exposed on the window portion extends from one end side of the window portion to the other end side, and has an enlarged end portion of the lead portion that is placed between two or more insulating layers and is formed with a larger width than a width of the lead portion in the window portion, at the other end side.

13 Claims, 13 Drawing Sheets

(51) Int. Cl.
*H05K 1/11* (2006.01)
*A61B 1/04* (2006.01)
*A61B 1/005* (2006.01)
*A61B 1/00* (2006.01)
*G02B 23/24* (2006.01)
*H05K 1/14* (2006.01)

(52) U.S. Cl.
CPC ...... *A61B 1/00163* (2013.01); *G02B 23/2484* (2013.01); *H04N 5/2252* (2013.01); *H05K 1/111* (2013.01); *H05K 1/144* (2013.01); *H05K 3/366* (2013.01); *G02B 23/243* (2013.01); *H05K 2201/041* (2013.01); *H05K 2201/09036* (2013.01)

(56) References Cited

U.S. PATENT DOCUMENTS

| | | | | |
|---|---|---|---|---|
| 8,462,464 | B1* | 6/2013 | Dunn | G11B 5/486 360/245.9 |
| 9,763,334 | B2* | 9/2017 | Ihara | H05K 3/3405 |
| 9,781,832 | B2* | 10/2017 | Kato | H05K 1/144 |
| 2002/0079124 | A1* | 6/2002 | Moden | H01L 23/49572 174/94 R |
| 2003/0026078 | A1 | 2/2003 | Komatsubara et al. | |
| 2007/0126524 | A1* | 6/2007 | Yagisawa | H05K 1/0219 333/33 |
| 2009/0277868 | A1* | 11/2009 | Ishii | H05K 3/242 216/13 |
| 2011/0224487 | A1 | 9/2011 | Ogawa | |
| 2013/0010392 | A1* | 1/2013 | Yamada | H05K 3/4007 360/245.9 |
| 2013/0342936 | A1* | 12/2013 | Nishiyama | G11B 5/486 360/244 |

FOREIGN PATENT DOCUMENTS

| | | |
|---|---|---|
| JP | 2006-094955 A | 4/2006 |
| JP | 2007-188979 A | 7/2007 |
| JP | 2011-192808 A | 9/2011 |
| JP | 2011-198402 A | 10/2011 |
| JP | 2013-098182 A | 5/2013 |
| JP | 2013-219468 A | 10/2013 |
| JP | 5426834 B2 | 2/2014 |
| JP | 2014-207371 A | 10/2014 |
| WO | WO 2014075758 A1 * | 5/2014 ........... A61B 1/0011 |

OTHER PUBLICATIONS

Japanese Office Action dated Sep. 20, 2016 issued in Japanese Patent Application No. 2016-531079.

* cited by examiner

US 10,039,437 B2

IMAGE PICKUP APPARATUS FOR ENDOSCOPE

CROSS REFERENCE TO RELATED APPLICATION

This application is a continuation application of PCT/JP2015/078085 filed on Oct. 2, 2015 and claims benefit of Japanese Application No. 2015-047445 filed in Japan on Mar. 10, 2015, the entire contents of which are incorporated herein by this reference.

BACKGROUND OF THE INVENTION

1. Field of the Invention

The present invention relates to an image pickup apparatus for an endoscope having a camera head that is connected to a proximal end portion of an endoscope including an insertion portion that is inserted into a body cavity and picks up an image of an inside of the body cavity.

2. Description of the Related Art

As an image pickup system for an endoscope configured by an endoscope including an insertion portion, a camera head that is provided attachably to and detachably from an eyepiece section provided at a proximal end portion of the endoscope via an adapter, a remote controller unit that is provided in a vicinity of the camera head and has a plurality of push switches or the like, a control unit or the like configured by including a control circuit or the like that controls an entire system, image pickup systems for endoscopes in various modes have been conventionally proposed by Japanese Patent No. 5426834 and the like.

In an image pickup system for an endoscope of this kind, a camera head is configured as an image pickup apparatus for an endoscope provided with an image pickup unit including an image pickup optical system, an image pickup device and the like inside the image pickup apparatus for an endoscope. A signal line for video is extended from the image pickup unit. The signal line for video is configured to be inserted through an inside of a camera cable extended from a control unit and extend to the control unit with a switch operation signal line that is extended from a remote controller unit, whereby electric connection of each of the camera head and the remote controller unit, and the control unit is ensured.

Inside the camera head in the conventional image pickup system for an endoscope including a configuration like this, a configuration is adopted, in which a relay board using a flexible printed circuit board or the like is provided between an image pickup unit and a camera cable including a signal line for video, with ease of assembly, ease of maintenance and the like taken into consideration.

In this case, as electric connection means between an image pickup board of the image pickup unit and the relay board, various connection means in a mode adopting a so-called flying lead structure that are disclosed in Japanese Patent Application Laid-Open Publication No. 2014-207371, Japanese Patent Application Laid-Open Publication No. 2013-98182, Japanese Patent Application Laid-Open Publication No. 2013-219468 and the like have been proposed.

Here, as the above described flying lead structure, the flying lead structure in a mode in which in a region at one end of the above described relay board, for example, only a conducting layer is left by removing an insulating layer in a region that is desired to be connected to land portions in the above described image pickup board. By using a relay board adopting the flying lead structure like this, the relay board can be also reliably connected to the land portions in a mode in which a plurality of narrow land pitches are arranged in the image pickup board of an image pickup device that is significantly reduced in size.

SUMMARY OF THE INVENTION

An image pickup apparatus for an endoscope of one aspect of the present invention includes a first circuit board on which a lead portion formed from a conducting layer is placed between two or more insulating layers, a window portion that is provided in the first circuit board, in which the insulating layers are hollowed out, and a part of the lead portion is exposed, and a second circuit board on which a circuit pattern is formed, the circuit pattern being fixed by soldering to the lead portion exposed on the window portion in a state in which the second circuit board is laid on the first circuit board, wherein the lead portion that is exposed on the window portion extends from one end side of the window portion to another end side, and has an enlarged end portion of the lead portion that is placed between the two or more insulating layers and is formed with a larger width than a width of the lead portion in the window portion, at the other end side.

DETAILED DESCRIPTION OF THE PREFERRED EMBODIMENT

Hereunder, the present invention will be described in accordance with an illustrated embodiment. The respective drawings for use in the following explanation are for schematic illustration, and in order to illustrate respective components in such sizes as to be recognizable on the drawings, a dimensional relation, scales and the like of respective members may be caused to differ for each of the components. Accordingly, the present invention is not limited to only the illustrated modes in regard with the numbers and quantities of the components described in the respective drawings, shapes of the components, ratios of the sizes of the components, relative positional relations of the respective components and the like.

[One Embodiment]

Figure 1:
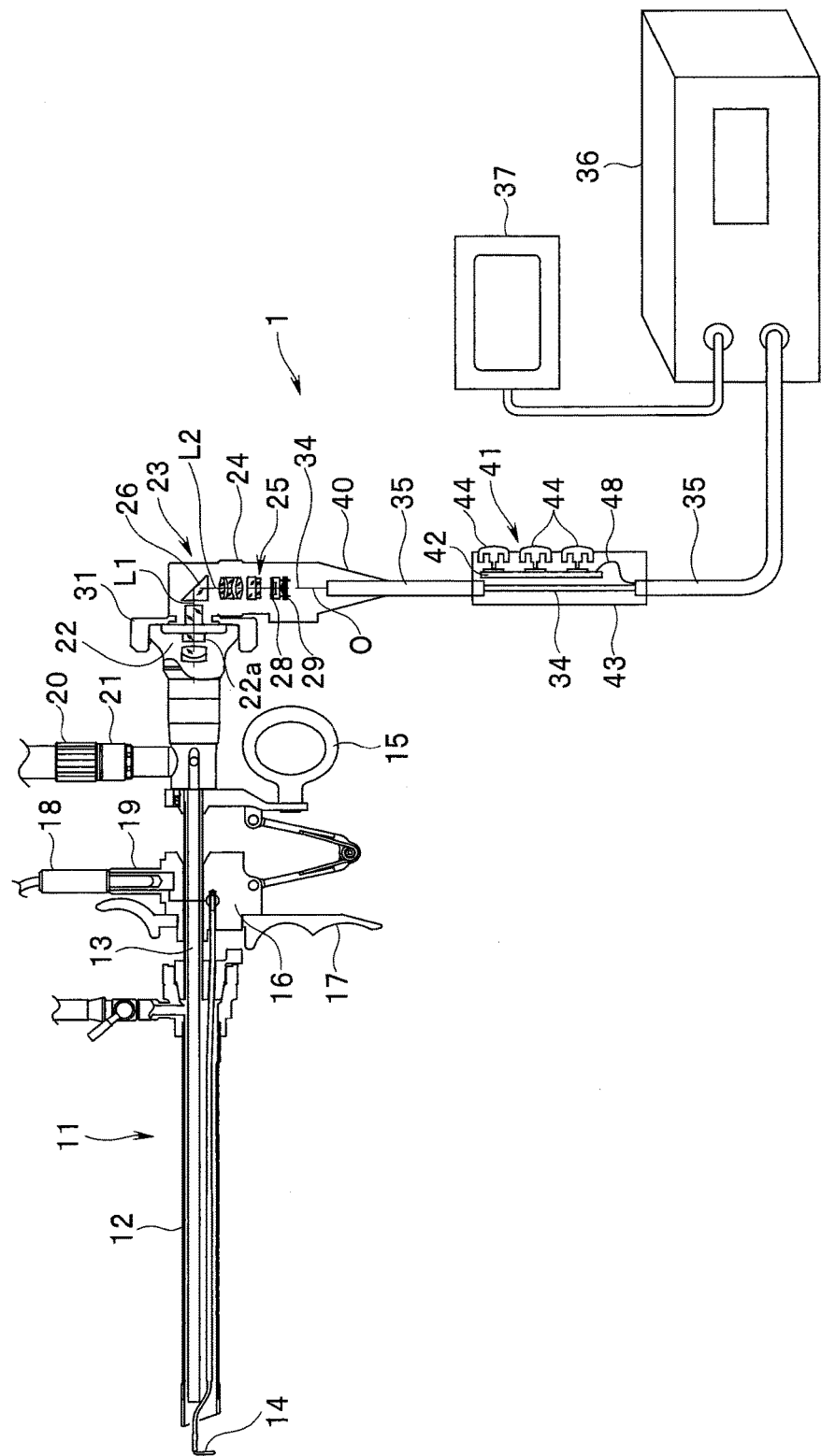
FIG. 1 is a general configuration view at a time of an image pickup apparatus for an endoscope of one embodiment of the present invention is applied to a resectoscope.
Figure 2:
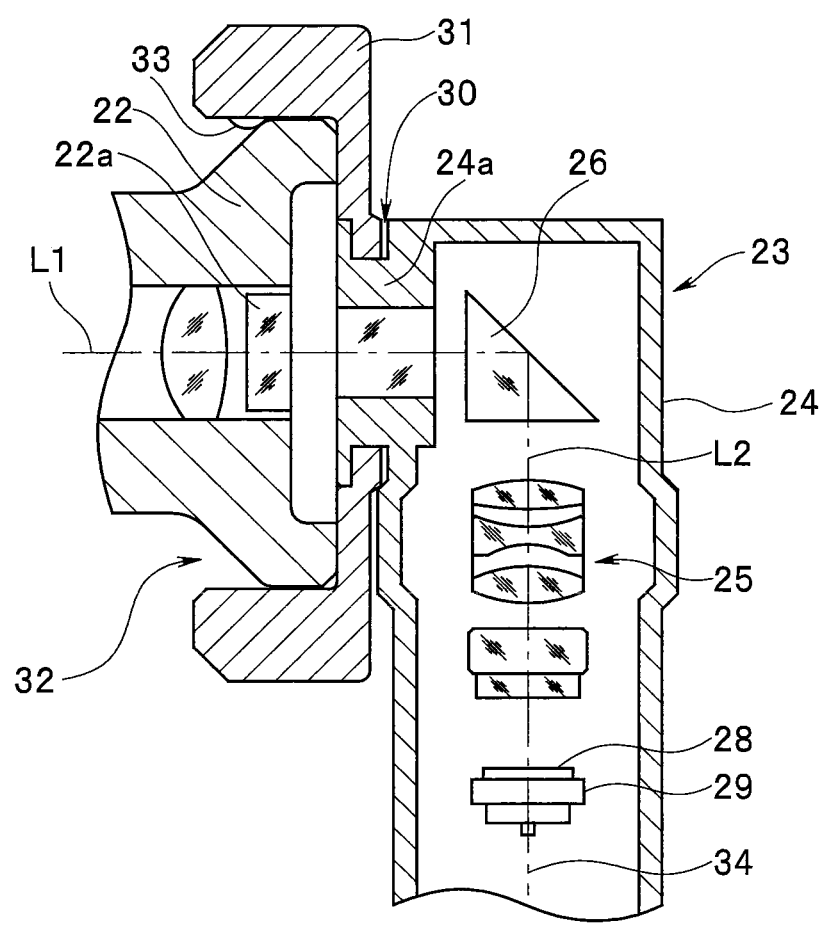
FIG. 2 is a sectional view illustrating an outline of an internal configuration of a camera head main body in the image pickup apparatus for an endoscope in FIG. 1.

FIG. 1 is a general configuration view at a time of an image pickup apparatus for an endoscope of one embodiment of the present invention being applied to a resectoscope. FIG. 2 is a sectional view illustrating an outline of an internal configuration of a camera head main body in the image pickup apparatus for an endoscope in FIG. 1.

First, a configuration of an entire system at the time of the image pickup apparatus for an endoscope of the present embodiment being applied to a resectoscope will be briefly described hereunder with use of FIG. 1 and FIG. 2.

An image pickup apparatus 1 for an endoscope is configured by a camera head main body 23, a remote controller unit 41, a control unit 36, a display apparatus 37 and the like. The image pickup apparatus 1 for an endoscope is used by being fitted to an endoscope apparatus such as a resectoscope 11. That is, an image pickup system for an endoscope is configured by the image pickup apparatus 1 for an endoscope and the endoscope apparatus (the resectoscope 11 or the like).

The resectoscope 11 as a rigid endoscope is provided with a sheath 12 as an insertion portion that is inserted into a body cavity. In the sheath 12, a distal end side portion of an optical viewing tube 13 and a distal end side portion of a resection electrode member 14 are inserted and disposed in parallel. A grasping handle 15 is provided at a hand side end portion of the sheath 12. The resection electrode member 14 is connected to a slide operation member 16 that is provided at the hand side end portion of the sheath 12.

The slide operation member 16 is provided with a finger grip operation handle 17 for an advancing and retreating operation. A finger is placed on the finger grip operation handle 17 and an operation of advancing and retreating the slide operation member 16 is performed, and thereby the resection electrode member 14 is advanced and retreated, whereby treatment of dissecting a biological tissue by a high-frequency current is enabled. At an upper end portion of the slide operation member 16, a power supply connector 19 for connecting a high-frequency power supply cord 18 that leads to a high-frequency power supply (not illustrated) is provided.

At a hand side end portion of the above described optical viewing tube 13, a light source connector 21 configured to connect a light guide cable 20 that is extended from an illuminating light source apparatus (not illustrated) is provided. Further, an eyepiece section 22 including an eyepiece lens 22a is provided at the hand side end portion of the optical viewing tube 13. The eyepiece section 22 is formed into a taper shape in which a rear side is enlarged in diameter. The camera head main body 23 that will be described later is attachably and detachably fitted to the eyepiece section 22.

The camera head main body 23 is a configuration section that is configured by a camera head casing 24, and an image pickup optical system 25 that is housed in the camera head casing 24, and configures a main configuration section of the image pickup apparatus for an endoscope of the present embodiment. The camera head casing 24 is formed into a substantially cylindrical shape, and inside the camera head casing 24, the above described image pickup optical system 25 and an image pickup device 29 such as a CCD are provided. Note that the above described image pickup optical system 25 is configured by a prism 26 as optical axis deflection means, an image forming optical system formed of a plurality of optical lenses, a filter 28 and the like. The filter 28 is disposed on a front surface of the image pickup device 29.

Further, as illustrated in FIG. 2, a cylindrical protruded portion 24a is formed on a side surface in an upper end portion of the camera head casing 24. A ring-shaped groove 30 is formed throughout an entire circumference on an outer circumferential surface of the protruded portion 24a. A mount member 31 for fitting the camera head main body 23 to the eyepiece section 22 is rotatably fitted in and connected to the ring-shaped groove 30.

That is, the ring-shaped groove 30 is provided with a very small gap so that the mount member 31 smoothly rotates, and free rotation of the camera head main body 23 is possible to the mount member 31. The mount member 31 is provided with a fitting hole 32 that is fitted onto the eyepiece section 22. A locking protrusion 33 that is locked to an outer circumferential portion of the eyepiece section 22 is protrusively provided inward on an inner circumferential surface of the fitting hole 32.

Consequently, according to the configuration, the camera head main body 23 is rotatable around an axis of the optical viewing tube 13, that is, with a first optical axis L1 as an axis, with respect to the eyepiece section 22 of the optical viewing tube 13 via the mount member 31. Further, the prism 26 inside the camera head main body 23 is disposed on the first optical axis L1. Here, a second optical axis L2 of the image pickup optical system 25 is orthogonal to the first optical axis L1 of the optical viewing tube 13.

That is, the second optical axis L2 of the image pickup optical system 25 extends in a vertical direction on an axis in the camera head main body 23, and the image forming optical system, the filter 28 and the image pickup device 29 of the image pickup optical system are sequentially placed to be along the second optical axis L2, from the prism 26 at an uppermost portion toward a lower side.

In this case, a gravity center O (refer to FIG. 1) of the camera head main body 23 is located below the first optical axis L1 (an axis of rotation of the camera head main body 23), and the camera head main body 23 is configured to rotate around the first optical axis L1 and to be always in an orientation in the vertical direction (an orientation in which the second optical axis L2 is along the vertical direction), irrespective of the optical viewing tube 13 rotating around the axis.

One end portion of a video signal line 34 is connected to the image pickup device 29. The video signal line 34 is connected to the control unit 36 via a camera cable 35. The display apparatus 37 such as a TV monitor is connected to the control unit 36.

By the configuration, a video signal expressing an endoscope image that is outputted from the image pickup device 29 is transmitted to the control unit 36 via the video signal line 34, and predetermined signal processing, for example, signal processing for generating video data for display suitable to display is performed by a signal processing circuit (not illustrated) in the control unit 36. The video data for display which is generated in this way is outputted to the display apparatus 37, and is shown as a visually recognizable endoscope image.

The camera cable 35 is configured to be in a mode in which an outer periphery of the camera cable 35 is covered with a net-shaped integrated shield wire (not illustrated), and an outer periphery of the integrated shield wire is further covered with an insulating coating film (not illustrated) or the like. Consequently, the above described video signal line 34 is shielded by the integrated shield wire. The camera cable 35 is extended from a lower end portion of the camera head casing 24. Here, a bend preventing tube 40 for preventing the extending camera cable 35 from bending is fitted to a lower end portion of the camera head casing 24.

As described above, the camera cable 35 has one end connected to the camera head casing 24, and has the other end connected to the control unit 36. Here, the remote controller unit 41 is interposed and placed in a site near the camera head main body 23, in a middle of the camera cable 35.

That is, the remote controller unit 41 is provided at a site near the camera head main body 23 in the middle of the camera cable 35 so that a surgeon easily grasps the grasping handle 15 at the optical viewing tube 13 with one hand, and operates the remote controller unit 41 with the other hand. By adopting the configuration, even when the remote controller unit 41 itself unintentionally moves by an operation force that is applied at the time of operating the remote controller unit 41, for example, the movement of the remote controller unit 41 is configured to be absorbed by the camera cable 35 and not to be transmitted to the camera head main body 23.

The remote controller unit 41 is configured by having a remote controller casing 43 in which a shield cylinder body is inserted, a printed circuit board 42, a plurality of push switches 44 and the like.

The remote controller casing 43 is a case member which is formed into a substantially cylindrical shape having openings at both end portions. The remote controller casing 43 is formed by using a light metal such as an aluminum. Inside the remote controller casing 43, the shield cylinder body (not illustrated) is inserted and disposed so as to be along an axial direction of the remote controller casing 43. The shield cylinder body is a shield member formed into a cylindrical shape from a light metal such as an aluminum. The camera cable 35 is inserted through an inside of the shield cylinder body. Here, the camera cable 35 is in a state in which the integrated shield wire and the insulating coating film are detached, in a portion that is covered with the above described shield casing.

That is, in a middle of the camera cable 35, a portion where the integrated shield wire and the insulating coating film are broken is provided in a region (in the shield cylinder body) inside the remote controller unit 41. The video signal line 34 is inserted through the inside of the shield cylinder body in an axial direction to reach the control unit 36. Further, an operation signal line 48 is extended from the printed circuit board 42 and is guided into the shield cylinder body, and thereafter reaches the control unit 36, as will be described later.

The printed circuit board 42 is fixed to an outer circumferential portion of the shield cylinder body. On the printed circuit board 42, a plurality of tact switches are mounted and disposed at predetermined spaces from one another. Further, the operation signal line 48 is extended from the printed circuit board 42. That is, the operation signal line 48 is connected to the printed circuit board 42 by soldering. The operation signal line 48 has an outer periphery covered with the integrated shield wire similarly to the above described video signal line 34. The operation signal line 48 is inserted through the camera cable 35 and extends to the above described control unit 36 to be connected to an internal circuit.

The plurality of push switches 44 are operation members that are provided to be exposed on an outer portion of the remote controller casing 43, and are for a surgeon to operate with use of fingers. The plurality of push switches 44 are disposed at sites facing the above described plurality of tact switches on the printed circuit board 42. By the configuration, a user can generate a desired control signal by performing a pressing operation of any one of the plurality of push switches 44. The control signal that is generated in this way is transmitted to the control unit 36 via the operation signal line 48 that is inserted through the inside of the camera cable 35.

Figure 3:
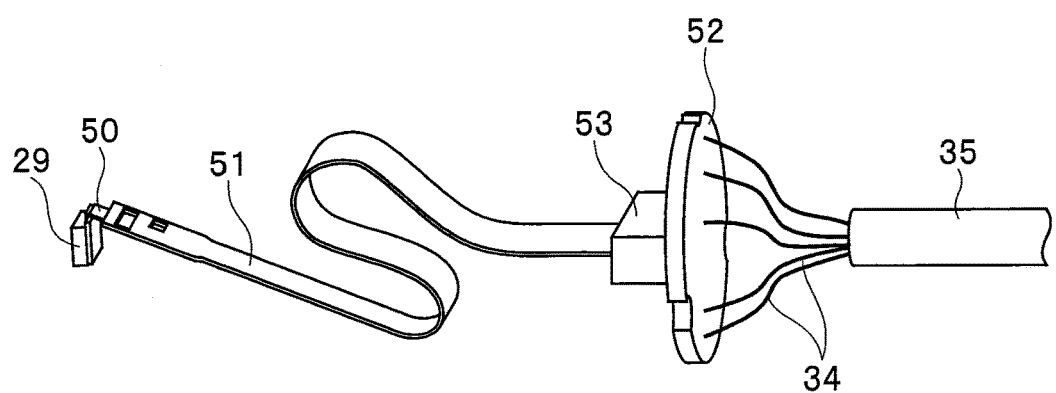
FIG. 3 is a schematic perspective view illustrating a configuration between an image pickup device and a camera cable, which is a main configuration section of the internal configuration of the camera head main body in the image pickup apparatus for an endoscope in FIG. 1.
Figure 4:
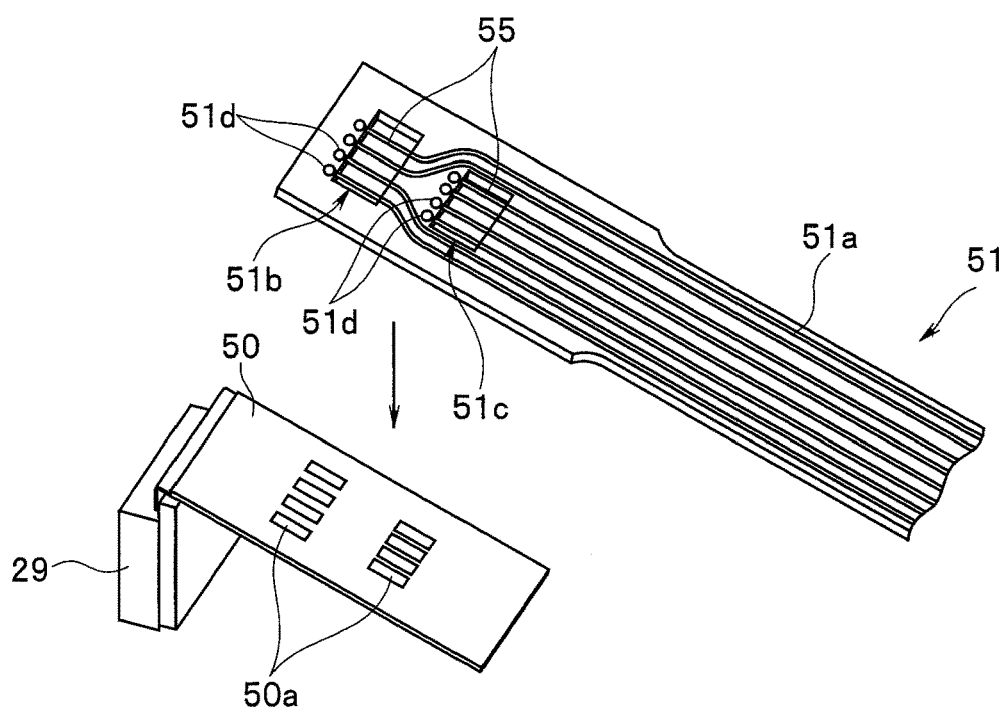
FIG. 4 is a main part exploded perspective view illustrating a configuration of a connection site of an image pickup board and a relay flexible board of the main configuration section illustrated in FIG. 3.
Figure 5:
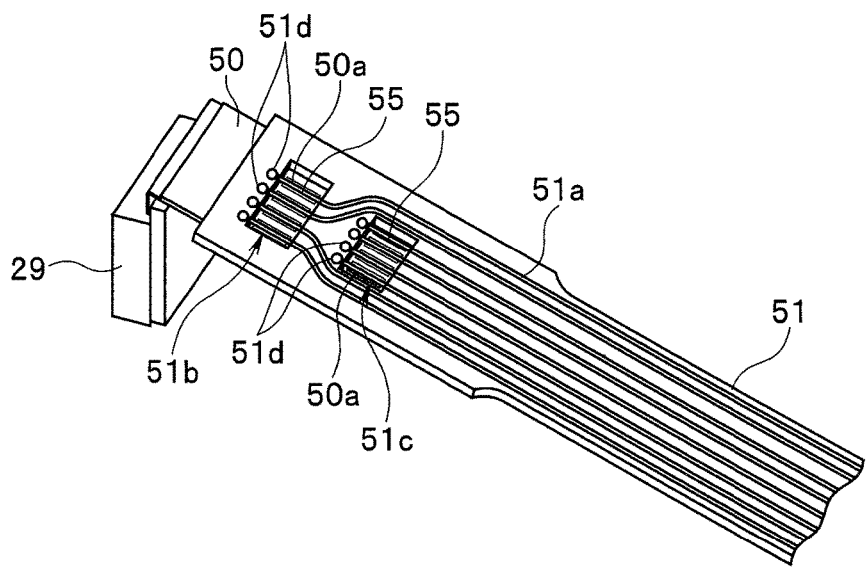
FIG. 5 is a perspective view illustrating a state in which both (the image pickup board and the relay flexible board) are fixed by soldering from a state in FIG. 4.
Figure 6:
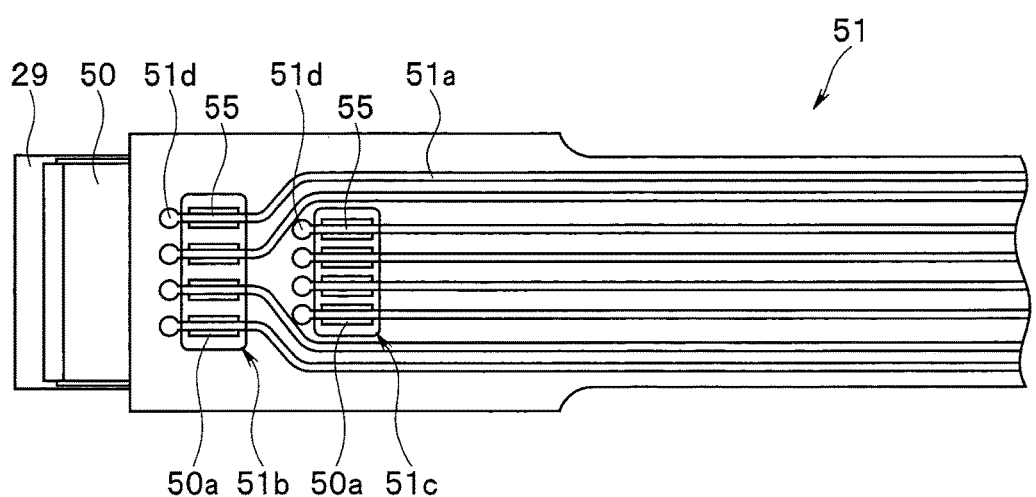
FIG. 6 is a main part enlarged plan view seen from a top surface of FIG. 5.

A main configuration section of an internal configuration of the camera head main body 23 in the image pickup apparatus 1 for an endoscope in the present embodiment which is configured as described above will be described hereunder with use of FIG. 3 to FIG. 6. FIG. 3 is a schematic perspective view illustrating a configuration between the image pickup device and the camera cable, which is the main configuration section of the internal configuration of the camera head main body 23 in the image pickup apparatus 1 for an endoscope of the present embodiment. Note that with respect to the main configuration section, illustration is omitted in FIG. 1. FIG. 4 is a main part exploded perspective view illustrating a configuration of a connection site of an image pickup board and a relay flexible board of the main configuration section illustrated in FIG. 3. FIG. 5 is a perspective view illustrating a state in which both (the image pickup board and the relay flexible board) are fixed by soldering from the state in FIG. 4. FIG. 6 is a main part enlarged plan view seen from a top surface of FIG. 5.

In an interior of the camera head main body 23 of the image pickup apparatus 1 for an endoscope, the image pickup device 29, an image pickup board 50 (a second circuit board), a relay flexible board 51 (a first circuit board), a flexible connector 53, a connector board 52, the video signal line 34, the camera cable 35 and the like are placed between the image pickup device 29 and the camera cable 35, as illustrated in FIG. 3.

The image pickup board 50 is a circuit board configured to have at least the image pickup device 29 mounted on the image pickup board 50 and have a circuit pattern that transmits an output signal from the image pickup device 29 formed on the image pickup board 50. The image pickup board 50 is formed by a rigid board, for example, and a plurality of land portions 50a (refer to FIG. 4) that are part of the circuit pattern corresponding to a flying lead structure of the relay flexible board 51 are formed on one surface of the image pickup board 50. The image pickup board 50 which is configured in this way has the land portions 50a (the circuit pattern) fixed by soldering to a conducting portion (described later) of the above described relay flexible board 51, in a state in which the image pickup board 50 is laid on the relay flexible board 51 (the first circuit board; a detailed configuration will be described later).

The relay flexible board 51 is a circuit board for connection and relay that is configured to ensure electric connection between the image pickup board 50 and the connector board 52, and to be able to cut off a connection state of both the image pickup board 50 and the connector board 52 easily. The relay flexible board 51 is configured by a flexible printed board or the like having flexibility, for example. Further, in the above described relay flexible board 51, a flying lead structure is formed in a predetermined region at one end. The relay flexible board 51 has one end connected to the above described image pickup board 50 by using the above described flying lead structure. The other end of the relay flexible board 51 is formed into a shape capable of being attachably and detachably connected to the flexible connector 53.

Here, the flying lead structure formed in the predetermined region at the one end of the relay flexible board 51 is specifically formed as follows.

A general flexible printed board is formed by a plurality of lead portions 51a that are formed from a conducting layer and form a circuit pattern, and a plurality of (two or more of) insulating layers that cover surfaces of the lead portions 51a. For the relay flexible board 51 which is applied to the present embodiment, a flexible printed board that is formed of a general configuration like this is used. In other words, the relay flexible board 51 is a circuit board in which the lead portions 51a formed from a conducting layer are placed between two or more insulating layers. Here, the relay flexible board 51 will be referred to as the first circuit board.

The present embodiment is formed in such a manner that in a predetermined region at one end of the relay flexible board 51, the insulating layers in regions desired to be connected to the land portions 50a of the image pickup board 50 are removed, and only the lead portions 51a that are conducting layers are left. Thereby, in the relay flexible board 51 which is applied to the present embodiment, window portions (51b, 51c) that are formed into hole shapes by removing the insulating layers are formed in the predetermined region at one end.

In other words, the above described window portions (51b, 51c) are provided in the relay flexible board 51 which is the above described first circuit board so that the insulating layers are hollowed out and part of the lead portions 51a are exposed. Here, sites exposed in the window portions 51b and 51c, of the lead portions 51a will be referred to as lead exposed portions 55. Further, in the present embodiment, an example is shown, in which the two window portions 51b and 51c are formed to be caused to correspond to the land portions 50a at two spots in the image pickup board 50.

In the above described two window portions 51b and 51c, part of the remaining conducting layer (the lead portion) is exposed in a shape of a plurality of lines. Here, the portions which are exposed on the window portions 51b and 51c, of the conducting layer will be referred to as the lead exposed portions 55 (refer to FIG. 4 and the like). In other words, the lead exposed portions 55 exposed on the window portions 51b and 51c are placed to extend from one end sides of the window portions 51b and 51c to the other end sides (tail end sides).

Further, tail end sites at the other end side to which the above described lead exposed portions 55 are connected, that are sites disposed at periphery portions of the above described window portions 51b and 51c, of the lead portions 51a, are placed between the two or more insulating layers. In the relay flexible board 51 which is applied to the present embodiment, the above described tail end sites are formed to have widths larger than width dimensions of the lead exposed portions 55 in the window portions 51b and 51c. The tail end site will be referred to as an enlarged end portion 51d of the lead portion 51a (refer to FIG. 6).

In other words, the lead exposed portions 55 that are exposed on the window portions 51b and 51c are disposed by extending from one end sides of the window portions 51b and 51c to the other end sides. The lead portion 51a at the other end side of the lead exposed portion 55 is configured to have the enlarged end portion 51d which is placed between two or more insulating layers, and is formed with a width larger than the widths of the lead exposed portions 55 in the window portions 51b and 51c.

The above descried enlarged end portion 51d in the present embodiment is specifically formed into a substantially circular shape having a diameter that is larger than the width dimensions of the above described lead portion 51a and the above described lead exposed portion 55. Thereby, the enlarged end portion 51d performs a function of locking the tail end site of the lead portion 51a onto the circuit board.

The flexible connector 53 is a connector portion that makes the other end of the relay flexible board 51 attachable and detachable. The flexible connector 53 is mounted on the connector board 52.

In the connector board 52, the flexible connector 53 is mounted on one surface, and respective one ends of a plurality of video signal lines 34 are connected to the other surface by soldering or the like. The plurality of video signal lines 34 are bundled, and are inserted through and disposed in the inside of the camera cable 35, finally reach the control unit 36, and have the other ends electrically connected to an internal circuit of the control unit 36, as described above.

In the image pickup apparatus 1 for an endoscope of the present embodiment which is configured in this way, the land portions 50a that are part of the circuit pattern of the image pickup board 50 are fixed by soldering to the lead exposed portions 55 that are exposed on the two window portions 51b and 51c of the relay flexible board 51 in the state in which the image pickup board 50 is laid on the relay flexible board 51 which is the first circuit board. Here, the image pickup board 50 will be referred to as the second circuit board.

As described above, according to the above described first embodiment, in the relay flexible board 51 which is the first circuit board, the shape of the enlarged end portion 51d is formed into a substantially circular shape with a diameter that is larger than the width dimensions of the lead portion 51a and the lead exposed portion 55.

By adopting the configuration like this, even when an external force load, stress by heat or the like to the board is applied at the time of fixing the land portions 50a of the image pickup board 50 and the lead exposed portions 55 of the relay flexible board 51 by soldering, for example, removal of the enlarged end portions 51d is prevented, and connection between both the boards (50, 51) can be reliably ensured.

Further, even when such an external force load occurs, that detaches the image pickup board 50 and the relay flexible board 51 from each other, after the above described fixing by soldering or the like is applied, removal of the enlarged end portions 51d and breakage of the lead exposed portions 55 can be prevented.

[First Modification]

In the aforementioned one embodiment, the shape of the enlarged end portion 51d is a substantially circular shape, but is not limited to the mode.

Figure 7:
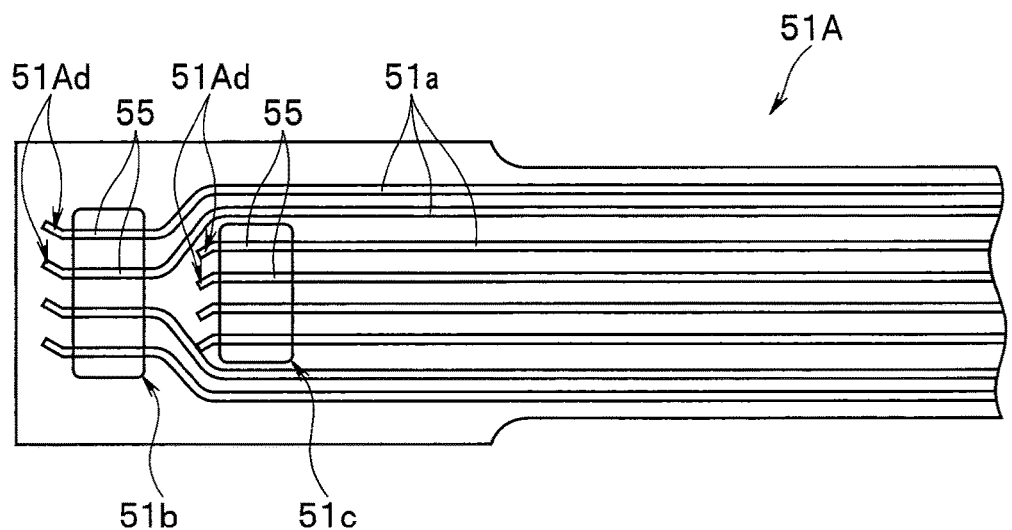
FIG. 7 is a main part enlarged plan view of a relay flexible board in a first modification of the one embodiment of the present invention.

For example, as another mode, as in a first modification of the relay flexible board illustrated in FIG. 7, a mode is conceivable, in which the tail end sites of the lead portions 51a are formed into bending shapes having predetermined inclined angles to axes of the lead exposed portions 55 that extend from one end sides to the other end sides of the window portions 51b and 51c, as shapes of enlarged end portions 51Ad in a relay flexible board 51A. That is, the tail end sites of the lead portions 51a are bent, whereby dimensions in width directions of the sites to the above described axes are set to be larger than width dimensions of the lead exposed portions 55.

[Second Modification]

Figure 8:
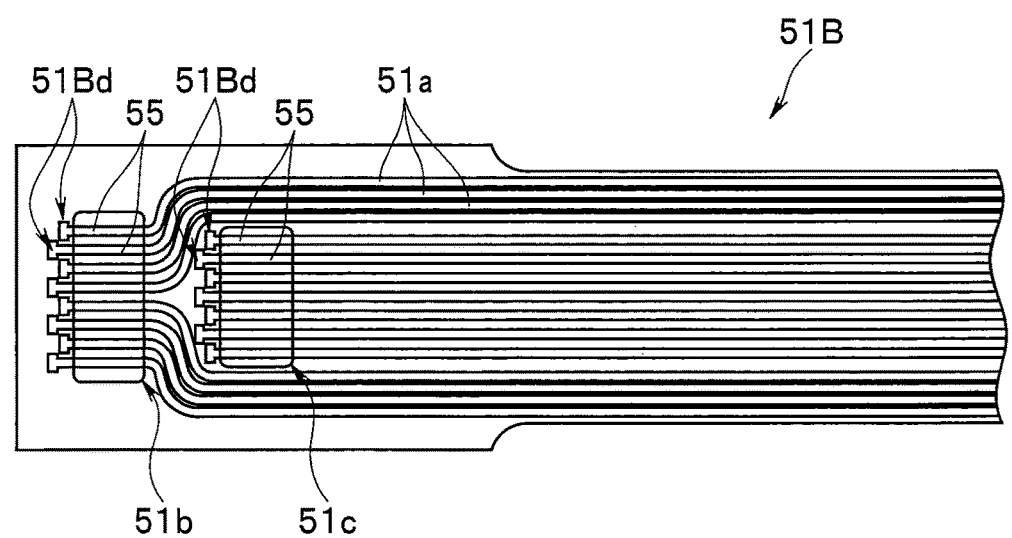
FIG. 8 is a main part enlarged plan view of a relay flexible board in a second modification of the one embodiment of the present invention.

Further, as another mode, as a second modification of the relay flexible board illustrated in FIG. 8, for example, a mode is conceivable, in which end portions are formed into T-shapes as shapes of enlarged end portions 51Bd in a relay flexible board 51B, and the respective enlarged end portions 51Bd which are closely adjacent to one another in the other end sides (the tail end sides) of the window portions 51b and 51c are disposed in a zigzag manner. That is, end portion shapes of the enlarged end portions 51Bd are formed into T-shapes, whereby width dimensions to axes of the lead exposed portions 55 are made larger than the widths of the lead exposed portions 55. In addition to this, the respective enlarged end portions 51Bd are disposed in a zigzag manner. By adopting a configuration like this, an additional effect of being able to be easily adapted to the relay flexible board 51B (the first circuit board) which is formed by a plurality of lead portions 51a having the enlarged end portions 51Bd being closely provided side by side at narrow pitches is obtained.

[Third Modification]

Note that another different configuration of the connection site of the image pickup board and the relay flexible board will be described hereunder, as the contrivance to apply no load to the flying lead section on the relay flexible board when an external force load that removes both the boards from each other occurs after assembly of the image pickup board and the relay flexible board by fixing by soldering or the like is finished.

Figure 9:
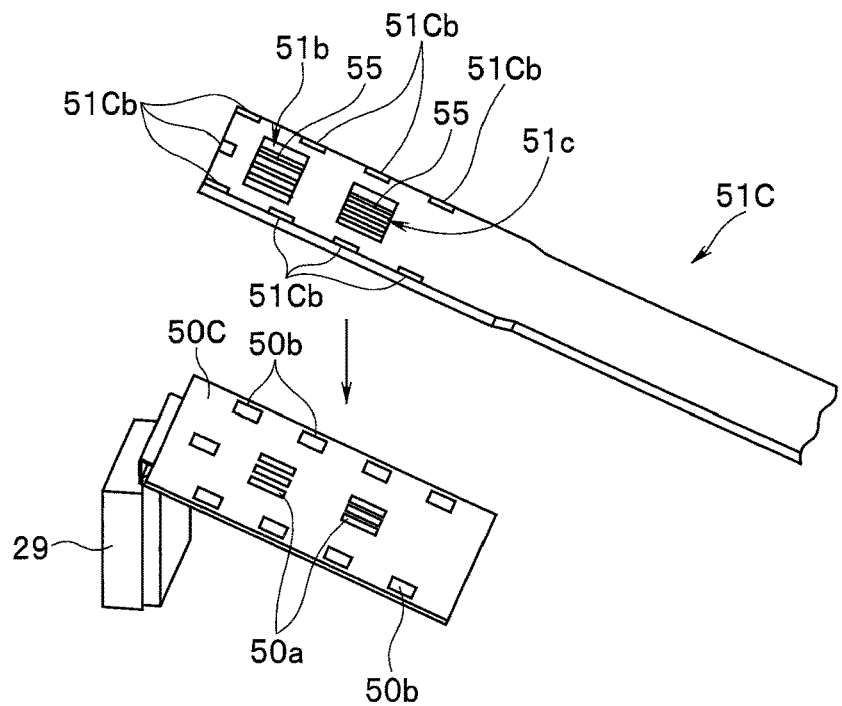
FIG. 9 is a main part exploded perspective view illustrating a configuration of a connection site of an image pickup board and a relay flexible board in a third modification of the one embodiment of the present invention.
Figure 10:
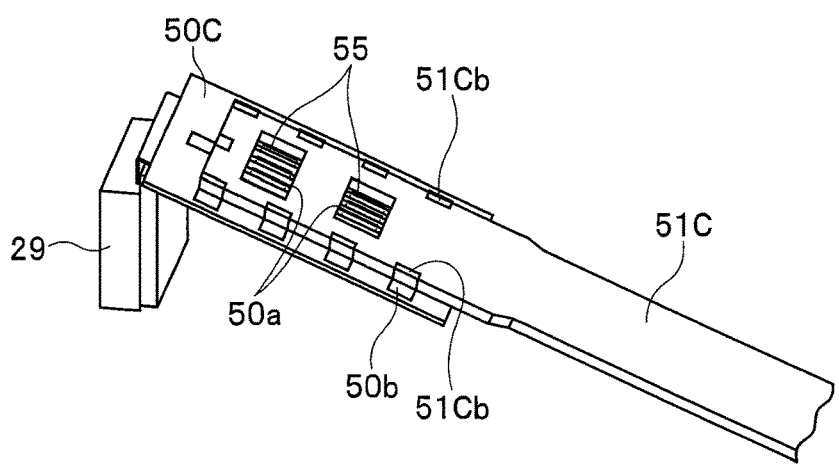
FIG. 10 is a perspective view illustrating a state in which the image pickup board and the relay flexible board in FIG. 9 are fixed by soldering.
Figure 11:
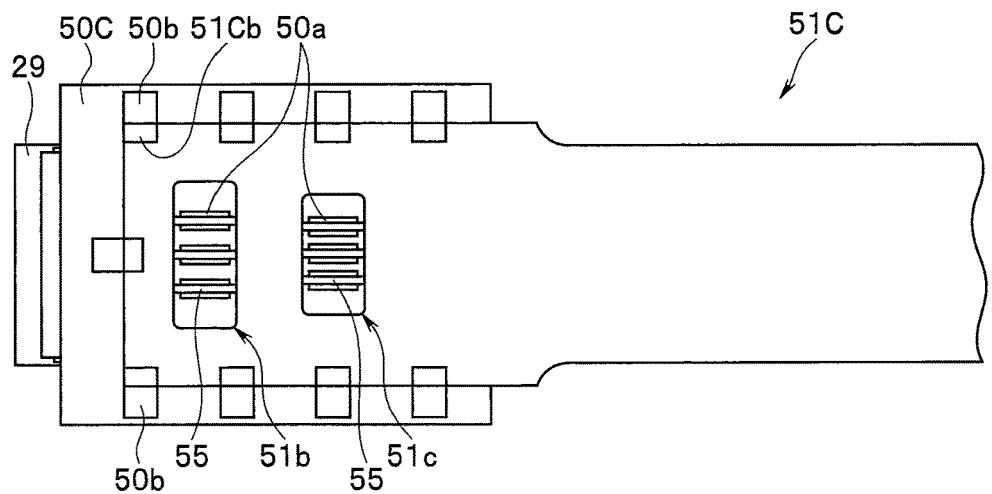
FIG. 11 is a main part enlarged plan view seen from a top surface of FIG. 10.

FIG. 9 to FIG. 11 are views illustrating a third modification of the present embodiment. Of FIGS. 9 to 11, FIG. 9 is a main part exploded perspective view illustrating a configuration of a connection site of an image pickup board and a relay flexible board. FIG. 10 is a perspective view illustrating a state in which the image pickup board and the relay flexible board in FIG. 9 are fixed by soldering. FIG. 11 is a main part enlarged plan view seen from a top surface of FIG. 10.

The present modification is configured by being provided with reinforcing solder portions 50b and 51Cb as means for reinforcing a bonded state of both the boards, in respective predetermined sites in a vicinity of a periphery portion of an image pickup board 50C and in a vicinity of a periphery portion at one end side of a relay flexible board 51C.

The reinforcing solder portions 50b on the image pickup board 50C are provided at a plurality of spots corresponding to the reinforcing solder portions 51Cb at the periphery portion of the relay flexible board 51C when the relay flexible board 51C is disposed by being laid on the image pickup board 50C.

The reinforcing solder portions 51Cb on the relay flexible board 51C are similarly provided at a plurality of spots corresponding to the reinforcing solder portions 50b at the periphery portion of the image pickup board 50C when the image pickup board 50C is disposed by being laid on the relay flexible board 51C.

The other configuration is the same as in the aforementioned one embodiment. Accordingly, lead portions in the present modification including the enlarged end portions are assumed to be placed in a mode similar to the above described one embodiment, although illustration of a plurality of lead portions (51a) that are formed from a conducting layer and form the circuit pattern is omitted in the relay flexible board 51C illustrated in FIG. 9 to FIG. 11.

When the image pickup board 50C and the relay flexible board 51C that are configured in this way are fixed and connected, the image pickup board 50C and the relay flexible board 51C are brought into a state in which the image pickup board 50C and the relay flexible board 51C are laid on each other, and the land portions 50a of the image pickup board 50C and the lead exposed portions 55 that are exposed on the two window portions 51b and 51c of the relay flexible board 51C are fixed by soldering as described in the aforementioned one embodiment.

In this state, in the present modification, the reinforcing solder portions 50b and the reinforcing solder portions 51Cb are further bonded by soldering as illustrated in FIG. 10 and FIG. 11. At this time, solder is provided in such a manner as to spread on side surface portions of the relay flexible board 51C, from the reinforcing solder portions 50b to the reinforcing solder portions 51Cb.

By adopting the configuration like this, resistance to the external force load that removes both the boards from each other can be further enhanced.

Note that in the above described third modification, the reinforcing solder portions 51Cb at the relay flexible board 51C side is configured to be provided at a surface (a surface which is exposed on an outer side at a time of the image pickup board 50C and the relay flexible board 51C being laid on each other) side in the periphery portion of the relay flexible board 51C.

Apart from the above mode, a mode as follows can be also conceivable as another mode of the third modification. That is, the reinforcing solder portions 51Cb at the relay flexible board 51C side may be configured to be provided at a back surface (a surface at a side facing the image pickup board 50C at the time of the image pickup board 50C and the relay flexible board 51C being laid on each other) side in the periphery portion of the relay flexible board 51C. When the configuration is adopted, the reinforcing solder portions 50b and 51Cb are provided at sites that face one another at the time of the image pickup board 50C and the relay flexible board 51C being laid on each other. When both the boards are fixed and connected, solder is spread into both the reinforcing solder portions 50b and 51Cb by adding heat from outer side surfaces of the relay flexible board 51C.

By adopting the configuration like this, resistance to the external force load that removes both the boards from each other can be also enhanced.

[Fourth Modification]

Figure 12:
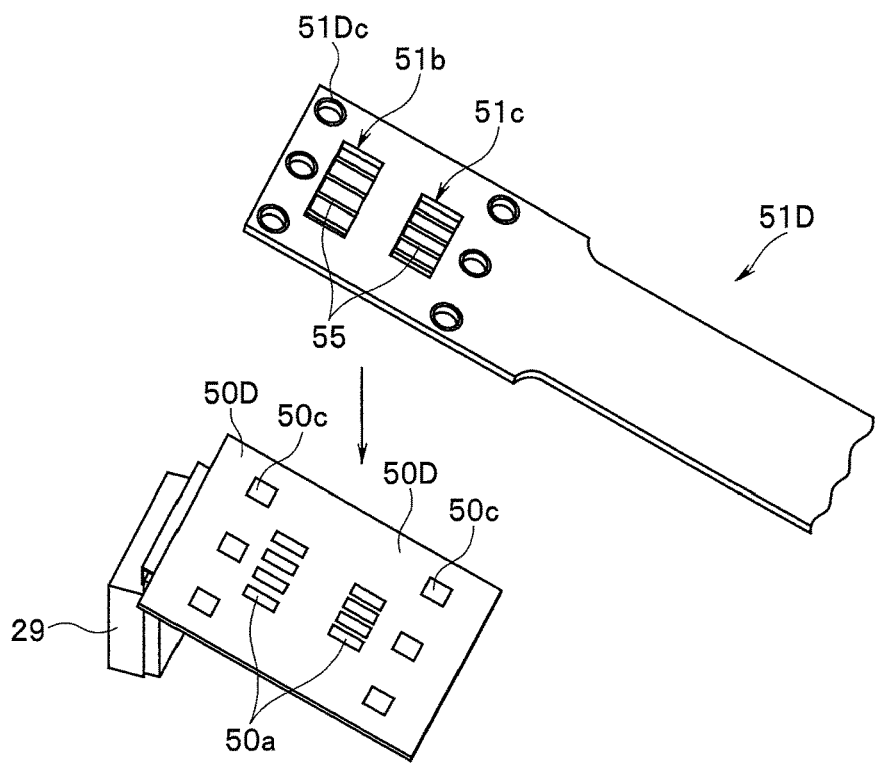
FIG. 12 is a main part exploded perspective view illustrating a configuration of a connection site of an image pickup board and a relay flexible board in a fourth modification of the one embodiment of the present invention.
Figure 13:
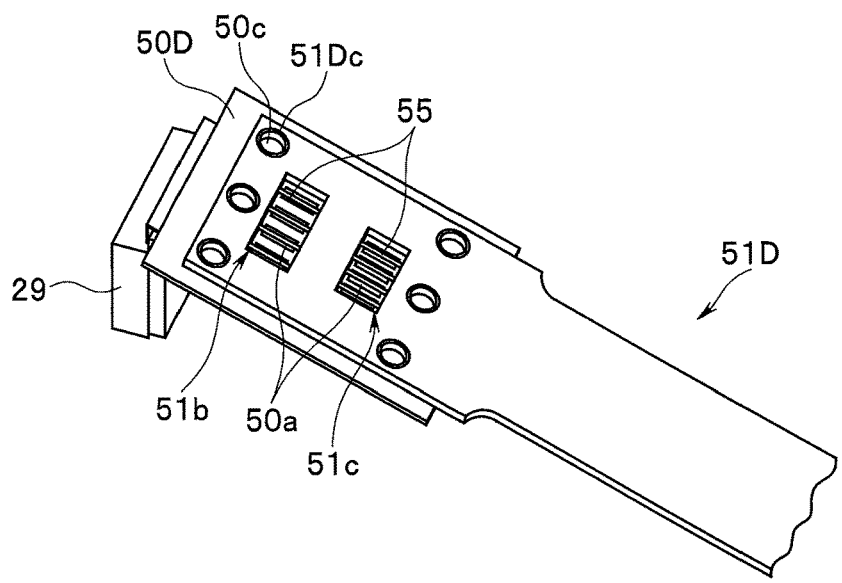
FIG. 13 is a perspective view illustrating a state in which the image pickup board and the relay flexible board in FIG. 12 are fixed by soldering.
Figure 14:
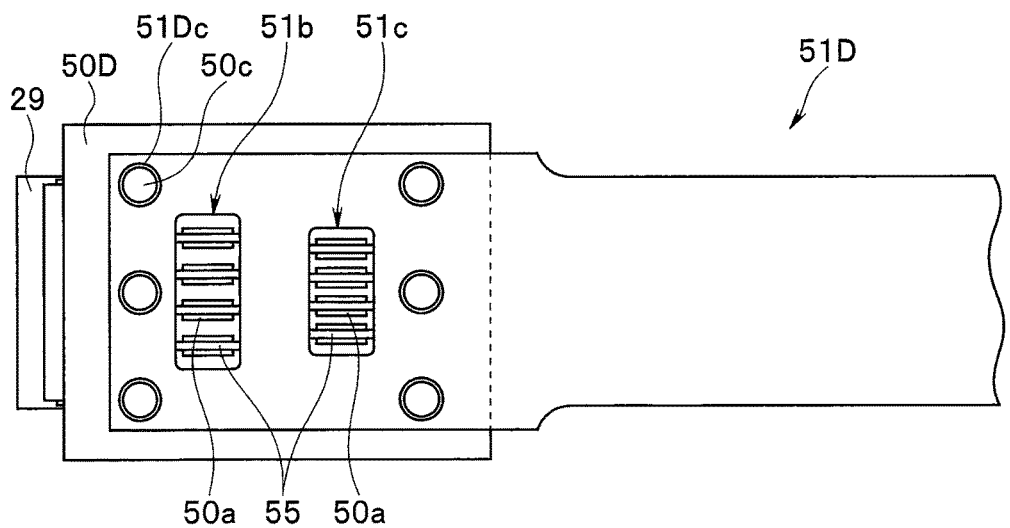
FIG. 14 is a main part enlarged plan view seen from a top surface of FIG. 13.

FIG. 12 to FIG. 14 are views illustrating a fourth modification of the present embodiment. Of FIGS. 12 to 14, FIG. 12 is a main part exploded perspective view illustrating a configuration of a connection site of an image pickup board and a relay flexible board. FIG. 13 is a perspective view illustrating a state in which the image pickup board and the relay flexible board in FIG. 12 are fixed by soldering. FIG. 14 is a main part enlarged plan view seen from a top surface of FIG. 13.

In the present modification, an image pickup board 50D is configured by being provided with reinforcing solder portions 50c, and a relay flexible board 51D is configured to be provided with through-holes 51Dc, as means for reinforcing a bonded state of both the boards, in respective predetermined sites in a vicinity of a periphery portion of the image pickup board 50D and in a vicinity of a periphery portion at one end side of the relay flexible board 51D.

The reinforcing solder portions 50c of the image pickup board 50D are provided at a plurality of spots that correspond to the through-holes 51Dc in the relay flexible board 51D when the relay flexible board 51D is disposed to be laid on the image pickup board 50D.

The through-holes 51Dc in the relay flexible board 51D are similarly provided at a plurality of spots that correspond to the reinforcing solder portions 50c at the periphery portion of the image pickup board 50D when the image pickup board 50D is disposed by being laid on the relay flexible board 51D.

The other configuration is the same as in the aforementioned one embodiment. Note that in the present modification, illustration of the circuit pattern (the lead portion) of the relay flexible board 51D illustrated in FIG. 12 to FIG. 14 is omitted, but the circuit pattern of the relay flexible board 51D is the same as in the above described one embodiment.

When the image pickup board 50D and the relay flexible board 51D which are configured as above are fixed and connected, the image pickup board 50D and the relay flexible board 51D are brought into a state in which the image pickup board 50D and the relay flexible board 51D are laid on each other, and the land portions 50a on the image pickup board 50D and the lead exposed portions 55 exposed on the two window portions 51b and 51c in the relay flexible board 51D are fixed by soldering, as described in the aforementioned one embodiment.

In this state, in the present modification, the reinforcing solder portions 50c and the through-holes 51Dc are further bonded by soldering as illustrated in FIG. 13 and FIG. 14.

By adopting the configuration like this, resistance to the external force load that removes both the boards from each other can be further enhanced as in the aforementioned third modification.

[Fifth Modification]

Figure 15:
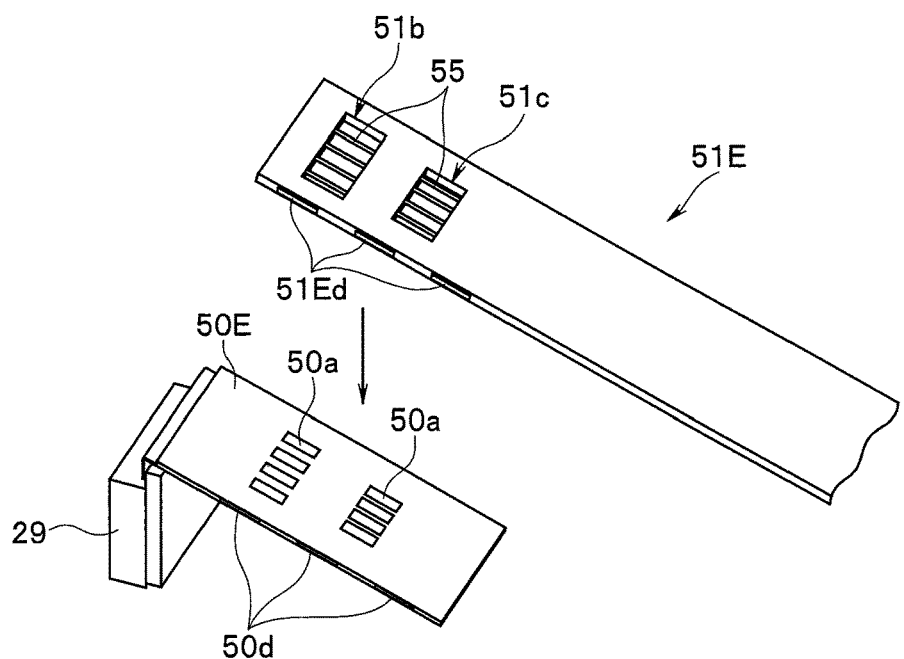
FIG. 15 is a main part exploded perspective view illustrating a configuration of a connection site of an image pickup board and a relay flexible board in a fifth modification of the one embodiment of the present invention.
Figure 16:
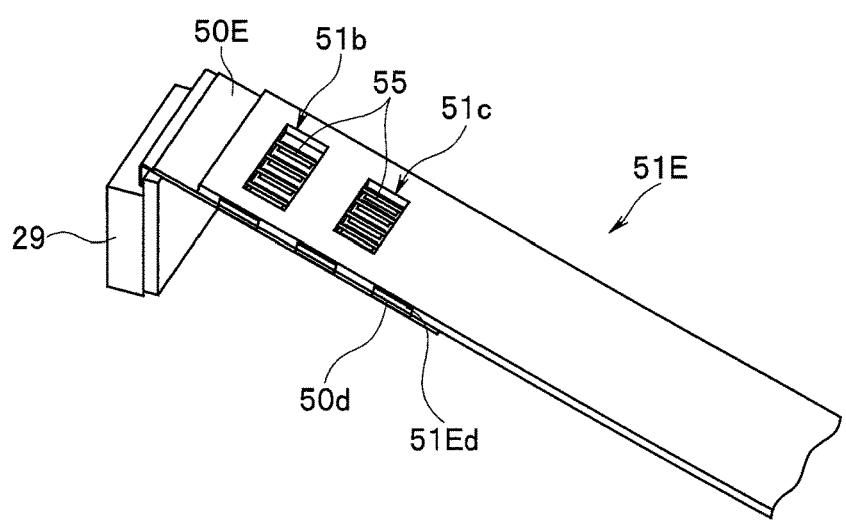
FIG. 16 is a perspective view illustrating a state in which the image pickup board and the relay flexible board in FIG. 15 are fixed by soldering.

FIG. 15 and FIG. 16 are views illustrating a fifth modification of the present embodiment. Of FIGS. 15 and 16, FIG. 15 is a main part exploded perspective view illustrating a configuration of a connection site of an image pickup board and a relay flexible board. FIG. 16 is a perspective view illustrating a state in which the image pickup board and the relay flexible board in FIG. 15 are fixed by soldering.

The present modification is configured by providing reinforcing solder portions 50d and 51Ed in respective predetermined sites on both side surfaces of a periphery portion of an image pickup board 50E, and both side surfaces of a periphery portion at one end side of a relay flexible board 51E, as means for reinforcing a bonded state of both the boards.

The reinforcing solder portions 50d of the image pickup board 50E are provided at a plurality of spots that correspond to the reinforcing solder portions 51Ed on both the side surfaces of the periphery portion of the relay flexible board 51E when the relay flexible board 51E is disposed by being laid on the image pickup board 50E.

The reinforcing solder portions 51Ed on the relay flexible board 51E are similarly provided at a plurality of spots that correspond to the reinforcing solder portions 50d on both the side surfaces of the periphery portion of the image pickup board 50E when the image pickup board 50E is disposed by being laid on the relay flexible board 51E.

The other configuration is the same as in the aforementioned one embodiment. Note that in the present modification, illustration of a circuit pattern (a lead portion) of the relay flexible board 51E illustrated in FIG. 15 and FIG. 16 is omitted, but the circuit pattern of the relay flexible board 51E is the same as in the above described one embodiment.

When the image pickup board 50E and the relay flexible board 51E which are configured in this manner are fixed and connected, the image pickup board 50E and the relay flexible board 51E are brought into a state in which the image pickup board 50E and the relay flexible board 51E are laid on each other, and the land portions 50a on the image pickup board 50E and the lead exposed portions 55 exposed on the two window portions 51b and 51c in the relay flexible board 51E are fixed by soldering, as described in the aforementioned one embodiment.

In this state, in the present modification, the reinforcing solder portions 50d and the reinforcing solder portions 51Ed are further bonded by soldering as illustrated in FIG. 16. That is, in the present modification, reinforcement bonding by soldering is performed on both the side surfaces of both the boards 50E and 51E.

By adopting the configuration like this, resistance to the external force load that removes both the boards from each other can be further enhanced.

[Sixth Modification]

The image pickup apparatus adopting the flying lead structure provided in the relay flexible board in bonding the image pickup board and the relay flexible board has a structure in which confirming a solder bonded state of the land portions in the image pickup board and the lead exposed portions in the relay flexible board by visual recognition, for example, in the flying lead section, is difficult, in addition to having a fear of removal of the lead portions, breakage of the lead exposed portions and the like due to an external force load and a load of a thermal stress or the like. Especially in recent years, the lead portions in a circuit pattern have tended to be disposed closely at narrow pitches, and therefore visual confirmation tends to be difficult.

Thus, instead of the flying lead structure, a configuration will be described hereunder, in which solder bonding of the land portions of the image pickup board and the lead exposed portions of the relay flexible board can be reliably performed, breakage and the like can be prevented, and the solder bonded state can be visually confirmed easily.

Figure 17:
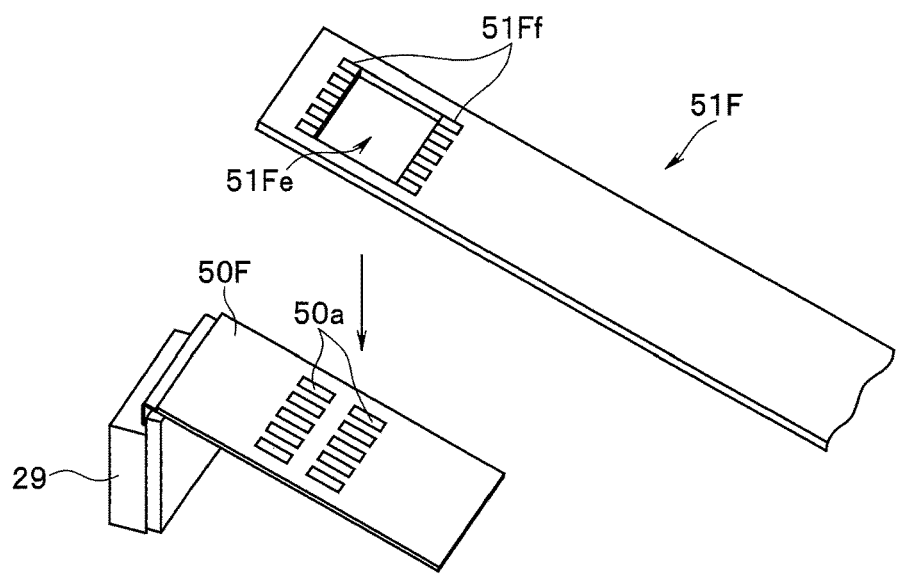
FIG. 17 is a main part exploded perspective view illustrating a configuration of a connection site of the image pickup board and a relay flexible board in a sixth modification of the one embodiment of the present invention.
Figure 18:
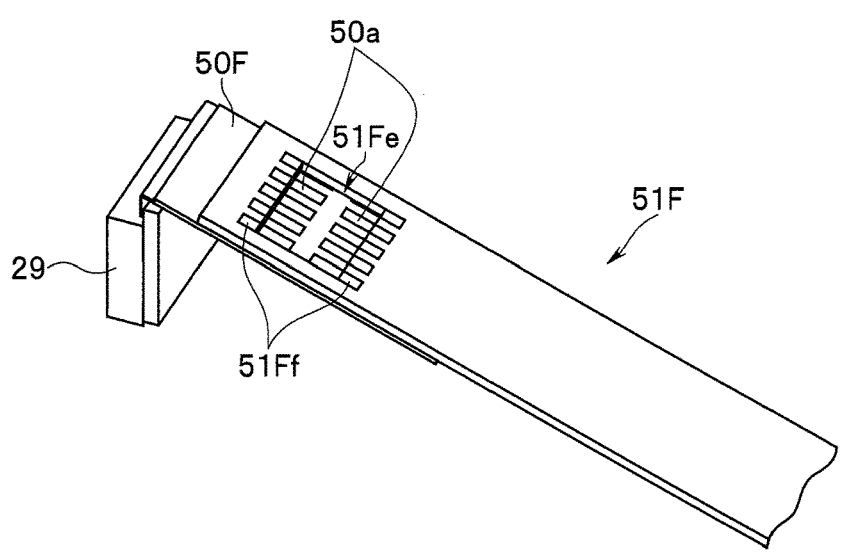
FIG. 18 is a perspective view illustrating a state (before fixing by soldering) in which the image pickup board and the relay flexible board in FIG. 17 are laid on each other.
Figure 19:
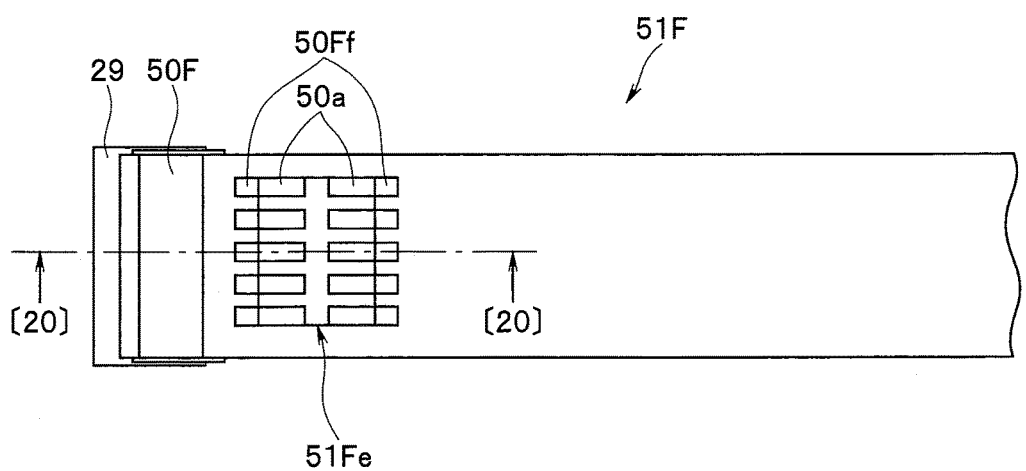
FIG. 19 is a main part enlarged plan view seen from a top surface of FIG. 18.
Figure 20:
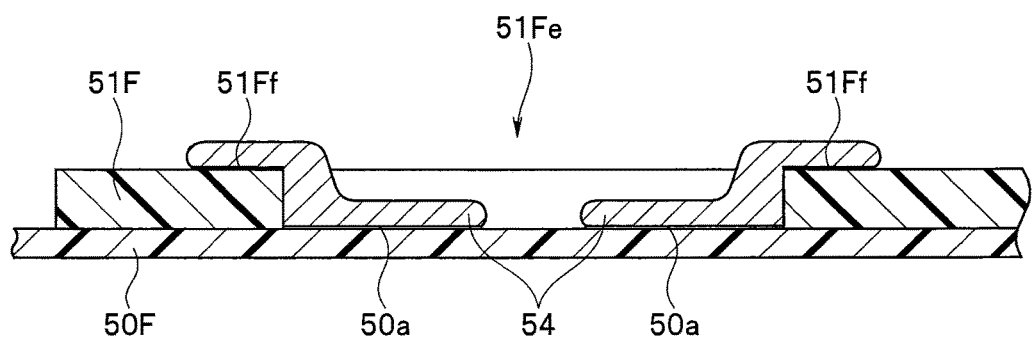
FIG. 20 is a main part enlarged sectional view along a line [20]-[20] in FIG. 19.
Figure 21:
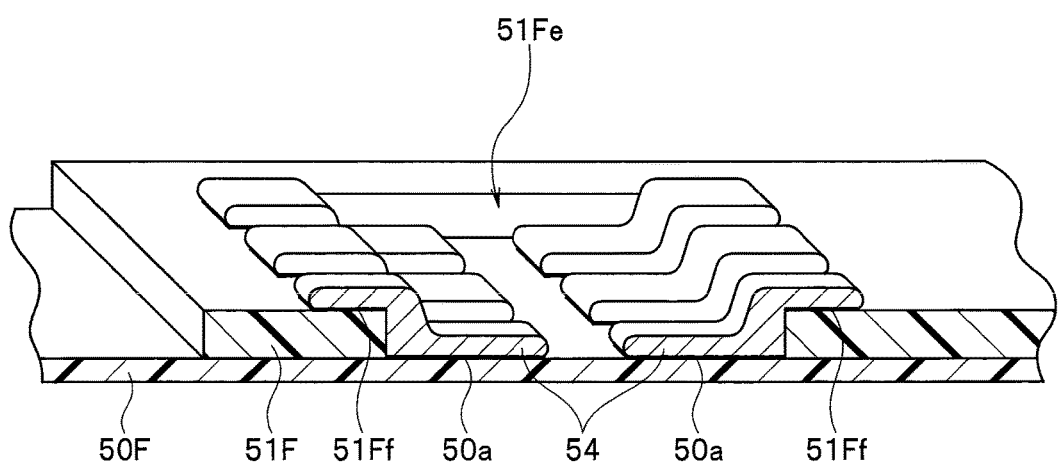
FIG. 21 is a main part enlarged sectional perspective view seen from diagonally above FIG. 20.

FIG. 17 to FIG. 21 are views illustrating a sixth modification of the present embodiment. Of FIG. 17 to FIG. 21, FIG. 17 is a main part exploded perspective view illustrating a configuration of a connection site of an image pickup board and a relay flexible board. FIG. 18 is a perspective view illustrating a state in which the image pickup board and the relay flexible board in FIG. 17 are laid on each other (before fixing by soldering). FIG. 19 is a main part enlarged plan view seen from a top surface of FIG. 18. FIG. 20 and FIG. 21 illustrate a state in which the image pickup board and the relay flexible board in FIG. 17 are laid on each other and solder fixing is applied. Of FIG. 20 and FIG. 21, FIG. 20 is a main part enlarged sectional view along line [20]-[20] in FIG. 19. FIG. 21 is a main part enlarged sectional perspective view seen diagonally above in FIG. 20.

In the present modification, in an image pickup board 50F, a plurality of land portions 50a that are part of a circuit pattern are formed on one surface of the image pickup board 50F, as in the aforementioned one embodiment. The land portions 50a are formed at sites corresponding to a window portion 51Fe in a relay flexible board 51F that will be described later.

In the relay flexible board 51F, the window portion 51Fe that is formed by hollowing out insulating layers is formed in a predetermined region at one end. The window portion 51Fe is formed in a site for exposing the land portions 50a of the image pickup board 50F when the above described image pickup board 50F and the relay flexible board 51F are laid on each other. Note that in the present modification, an example is shown, in which the relay flexible board 51F is formed to have the single window portion 51Fe.

Further, land portions 51Ff are provided at a plurality of sites on which the land portions 50a of the image pickup board 50F are laid, in an inner periphery portion of the above described window portion 51Fe, when the above described image pickup board 50F and the relay flexible board 51F are laid on each other and are respectively positioned in a predetermined position. That is, the land portions 50a on the image pickup board 50F side and the land portions 51Ff on the relay flexible board 51F side are disposed to be laid on one another when the image pickup board 50F and the relay flexible board 51F are laid on each other. At this time, the land portions 50a (the circuit pattern) on the image pickup board 50F are exposed in a range of the window portion 51Fe being projected, in a direction in which the window portion 51Fe of the relay flexible board 51F is hollowed out. A state at this time is a state illustrated in each of FIG. 18 and FIG. 19. In this state, soldering is performed in such a manner as to connect both the land portions 51Ff and 50a from the land portions 51Ff on the relay flexible board 51F side to the land portions 50a on the image pickup board 50F side, and thereby both the boards 50F and 51F are bonded. Consequently, as illustrated in FIG. 20 and FIG. 21, the land portions 51Ff and the land portions 50a are electrically connected by solder 54.

The other configuration is the same as in the aforementioned one embodiment. Note that in the present modification, illustration of the circuit pattern (the lead portions) on the relay flexible board 51F illustrated in FIG. 17 to FIG. 21 is also omitted, but the circuit pattern of the relay flexible board 51F is the same as in the above described one embodiment.

Even when the mode which is replaced with the flying lead structure is adopted, the land portions 50a on the image pickup board 50F and the land portions 51Ff on the relay flexible board 51F can be also connected reliably. Further, quality of the solder bonded state can be easily confirmed by visually confirming a fillet.

[Seventh Modification]

Figure 22:
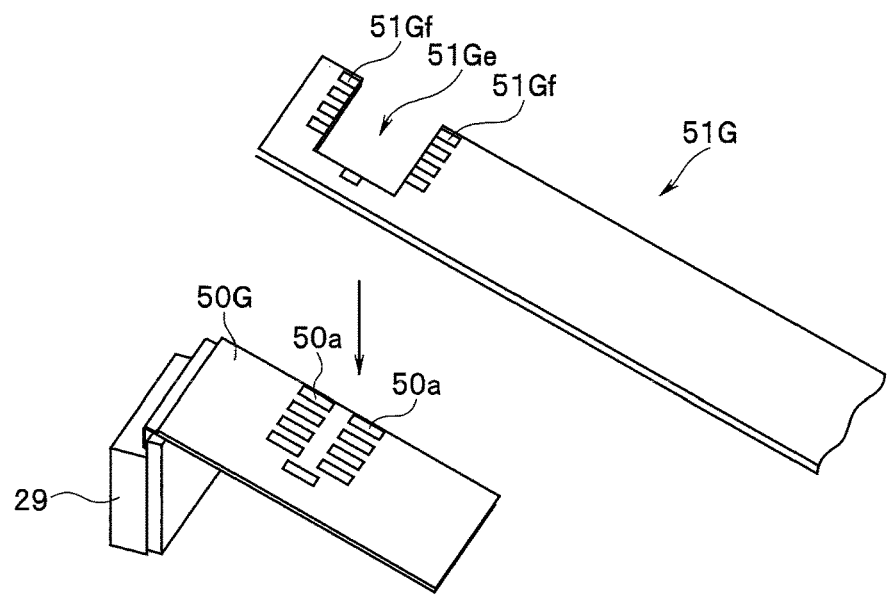
FIG. 22 is a main part exploded perspective view illustrating a configuration of a connection site of an image pickup board and a relay flexible board in a seventh modification of the one embodiment of the present invention.
Figure 23:
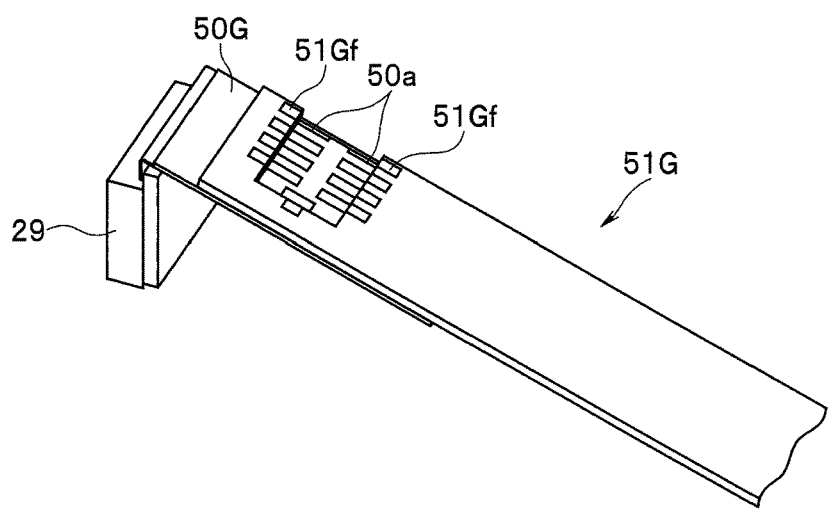
FIG. 23 is a perspective view illustrating a state (before fixing by soldering) in which the image pickup board and the relay flexible board in FIG. 22 are laid on each other.

FIG. 22 and FIG. 23 are views illustrating a seventh modification of the present embodiment. Of FIG. 22 and FIG. 23, FIG. 22 is a main part exploded perspective view illustrating a configuration of a connection site of an image pickup board and a relay flexible board. FIG. 23 is a perspective view illustrating a state (before fixing by soldering) in which the image pickup board and the relay flexible board in FIG. 22 are laid on each other.

In the present modification, on an image pickup board 50G, a plurality of land portions 50a that are part of a circuit pattern are formed on one surface of the image pickup board 50G, as in the aforementioned one embodiment. The land portions 50a are formed at sites corresponding to a cutout window portion 51Ge of a relay flexible board 51G that will be described later. Note that in the present modification, the land portions 50a on the image pickup board 50G are provided so that a number and disposition of the land portions 50a are made to differ from the numbers and the dispositions in the examples illustrated in the above described one embodiment and the respective modifications. That is, as illustrated, the plurality of land portions 50a on the image pickup board 50G are disposed in a region to one side surface as a whole.

In correspondence with the above, on the relay flexible board 51G, the cutout window portion 51Ge formed by cutting out insulating layers in a predetermined region at one end is formed. The cutout window portion 51Ge is formed in a site for exposing the plurality of land portions 50a on the image pickup board 50G when the above described image pickup board 50G and the relay flexible board 51G are laid on each other. Specifically, for example, the cutout window portion 51Ge is in a mode in which a region corresponding to the disposition region of the above described plurality of land portions 50a is cut out toward an inner side from a one side surface of the relay flexible board 51G. Note that in the present modification, an example is shown, in which the relay flexible board 51G is formed to have the single cutout window portion 51Ge.

The above described cutout window portion 51Ge is provided with a plurality of land portions 51Gf at predetermined sites of an inner periphery portion of the cutout window portion 51Ge, as in the above described sixth modification. Here, placement positions of the plurality of land portions 51Gf are sites on which the land portions 50a on the image pickup board 50G are laid when the above described image pickup board 50G and the relay flexible board 51G are laid on each other.

It is as in the aforementioned sixth embodiment that the land portions 50a on the image pickup board 50G side and the land portions 51Gf on the relay flexible board 51G side are disposed to be laid on one another when the image pickup board 50G and the relay flexible board 51G are laid on each other by the configuration as above. A state at this time is a state illustrated in each of FIG. 22 and FIG. 23. In this state, both the boards 50G and 51G are bonded by performing soldering in such a manner as to connect both the land portions 51Gf and 50*a*. Consequently, the land portions 51Gf and the land portions 50*a* are electrically connected by solder. Note that illustration of a bonded state by solder is omitted in FIG. 22 and FIG. 23, but in the present modification, the bonded state of both the boards is also substantially similar to the bonded state in FIG. 20 and FIG. 21 that are used in the above described sixth modification.

The other configuration is as in the aforementioned one embodiment. Note that in the present modification, illustration of a circuit pattern (lead portions) on the relay flexible board 51G illustrated in FIG. 22 and FIG. 23 is also omitted, but the circuit pattern is the same as in the above described one embodiment.

In this way, according to the configuration of the present modification, a similar effect to the effect of the above described sixth modification can be obtained. Further, in the present modification, solder bonding of both the boards 50G and 51G is performed in the cutout window portion 51Ge in the mode having an opening at the one side portion, and therefore visual confirmation of a fillet for confirming the solder bonded state can be carried out more easily.

Note that it is possible to apply the configurations shown in the third, the fourth and the fifth modifications described above to the sixth and the seventh modifications described above. According to the configurations, contribution can be made to further enhancement of resistance to an external force load that removes the image pickup board and the relay flexible board from each other.

Further, as the contrivance for enhancing the resistance to the external force load, means as follows is further conceivable in addition to the one embodiment and the modes of the respective modifications described above.

For example, after the image pickup board and the relay flexible board are solder bonded by the aforementioned means, potting work using a resin or the like may be applied in such a manner as to cover an entire bonded site. Further, apart from the above, a housing that covers an entire bonded site of an image pickup board and a relay flexible board is prepared, the bonded site is covered with the above described housing after both the boards are solder bonded, and potting work that fills an inside of the housing with a resin or the like may be applied.

By applying potting work using a resin or the like to the bonded site of both the boards in this way, contribution can be made to enhancement of resistance to an external force load. Further, an effect of being capable of contributing to enhancement in humidity resistance is obtained by the above described potting work.

The present invention is not limited to the aforementioned embodiment, and it is possible to carry out various modifications and applications within a range without departing from the gist of the invention as a matter of course. Further, the above described embodiment includes inventions at various stages, and various inventions can be extracted by arbitrariness combination in the plurality of components which are disclosed. For example, even when some components are deleted from all the components shown in the above described one embodiment, if the problem to be solved by the invention can be solved, and the effect of the invention is obtained, the configuration from which the components are deleted can be extracted as the invention. Further, components in different embodiments may be arbitrarily combined. The invention is not limited by a specific aspect of carrying out the invention except that the invention is limited by the accompanying claims.

INDUSTRIAL APPLICABILITY

The present invention can be applied to not only an endoscope control apparatus in a medical field but also an endoscope control apparatus in an industrial field.

What is claimed is:

1. An image pickup apparatus for an endoscope comprising:
   a first circuit board on which a plurality of leads formed from a conducting layer are placed between two or more insulating layers;
   a window that is provided in the first circuit board, in which the insulating layers are hollowed out in a thickness direction of the first circuit board, and a part of each of the leads is exposed through the window; and
   a second circuit board on which a circuit pattern is formed, the circuit pattern being fixed by soldering to the part of each of the leads lead portions exposed in the window in a state in which the second circuit board is laid on the first circuit board,
   wherein the part of each of the leads that is exposed in the window extends from a first side of the window to a second side of the window,
   the second side of the window being closer to a first end of the first circuit board than the first side of the window,
   the first end of the first circuit board overlapping the second circuit board when viewed from the thickness direction,
   enlarged ends of the plurality of leads being positioned between the second side of the window and the first end of the first circuit board,
   each of the enlarged ends having a width larger than a width of a corresponding lead in the window when viewed from the thickness direction; and
   each of the enlarged ends are circular enlarged ends when viewed in the thickness direction.

2. An image pickup apparatus for an endoscope comprising:
   a first circuit board on which a plurality of leads formed from a conducting layer are placed between two or more insulating layers;
   a window that is provided in the first circuit board, in which the insulating layers are hollowed out in a thickness direction of the first circuit board, and a part of each of the leads is exposed through the window; and
   a second circuit board on which a circuit pattern is formed, the circuit pattern being fixed by soldering to the part of each of the leads exposed in the window in a state in which the second circuit board is laid on the first circuit board,
   wherein the part of each of the leads that is exposed in the window extends from a first side of the window to a second side of the window,
   the second side of the window being closer to a first end of the first circuit board than the first side of the window,
   the first end of the first circuit board overlapping the second circuit board when viewed from the thickness direction,
   enlarged ends of the plurality of leads being positioned between the second side of the window and the first end of the first circuit board, each of the enlarged ends having a width larger than a width of a corresponding lead in the window when viewed from the thickness direction; and each of the enlarged ends are T-shaped enlarged ends when viewed in the thickness direction.

3. The image pickup apparatus for an endoscope according to claim 1, further comprising first reinforcing solder portions provided in a periphery portion of the first circuit board and second reinforcing solder portions provided in a periphery portion of the second circuit board, for reinforcing a bonded state of the first circuit board to the second circuit board by solder, and the first reinforcing solder portions of the first circuit board and the second reinforcing solder portions of the second circuit board are arranged at positions facing each other when the second circuit board is laid on the first circuit board.

4. An image pickup apparatus for an endoscope comprising:

a first circuit board on which a plurality of leads formed from a conducting layer are placed between two or more insulating layers;

a window that is provided in the first circuit board, in which the insulating layers are hollowed out in a thickness direction of the first circuit board, and a part of each of the leads is exposed through the window; and a second circuit board on which a circuit pattern is formed, the circuit pattern being fixed by soldering to the part of each of the leads exposed on the window in a state in which the second circuit board is laid on the first circuit board, wherein the part of each of the leads that is exposed on the window extends from a first side of the window to a second side of the window, the second side of the window being closer to a first end of the first circuit board than the first side of the window, the first end of the first circuit board overlapping the second circuit board when viewed from the thickness direction, enlarged ends of the plurality of leads being positioned between the second side of the window and the first end of the first circuit board, each of the enlarged ends extending further in a width direction than an extent of a corresponding lead in the width direction; and wherein each of the enlarged ends is formed in a bending shape having an inclination angle to an axis of the part of each of the plurality of leads extending from the first side of the window to the second side of the window.

5. The image pickup apparatus for an endoscope according to claim 2, wherein in the first circuit board, the plurality of leads are provided side by side, and each of the plurality of leads respectively have the enlarged end, and placement positions at the second side, of the enlarged ends adjacent to one another are disposed in a zigzag manner.

6. The image pickup apparatus for an endoscope according to claim 1, wherein the part of each of the leads exposed through the window has a uniform thickness from the first side of the window to the second side of the window.

7. The image pickup apparatus for an endoscope according to claim 4, wherein the part of each of the leads exposed through the window has a uniform thickness from the first side of the window to the second side of the window.

8. The image pickup apparatus for an endoscope according to claim 2, wherein the part of each of the leads exposed through the window has a uniform thickness from the first side of the window to the second side of the window.

9. The image pickup apparatus for an endoscope according to claim 1, wherein:

the window comprises a first window and a second window, with the first window being closer to the first end than the second window;

the part of the leads exposed through the window comprises a first part of a first set of the plurality of leads being exposed through the first window and a second part of a second set of the plurality of leads being exposed through the second window;

the circuit portion comprising a first circuit portion corresponding to the first part of the first set of the plurality of leads and a second circuit portion corresponding to the second part of the second set of the plurality of leads; and a portion of each of the first set of the plurality of leads not exposed through the first window are routed around the second window.

10. The image pickup apparatus for an endoscope according to claim 4, wherein:

the window comprises a first window and a second window, with the first window being closer to the first end than the second window;

the part of the leads exposed through the window comprises a first part of a first set of the plurality of leads being exposed through the first window and a second part of a second set of the plurality of leads being exposed through the second window;

the circuit portion comprising a first circuit portion corresponding to the first part of the first set of the plurality of leads and a second circuit portion corresponding to the second part of the second set of the plurality of leads; and a portion of each of the first set of the plurality of leads not exposed through the first window are routed around the second window.

11. The image pickup apparatus for an endoscope according to claim 2, wherein:

the window comprises a first window and a second window, with the first window being closer to the first end than the second window;

the part of the leads exposed through the window comprises a first part of a first set of the plurality of leads being exposed through the first window and a second part of a second set of the plurality of leads being exposed through the second window;

the circuit portion comprising a first circuit portion corresponding to the first part of the first set of the plurality of leads and a second circuit portion corresponding to the second part of the second set of the plurality of leads; and a portion of each of the first set of the plurality of leads not exposed through the first window are routed around the second window.

12. The image pickup apparatus for an endoscope according to claim 4, further comprising first reinforcing solder portions provided in a periphery portion of the first circuit board and second reinforcing solder portions provided in a periphery portion of the second circuit board, for reinforcing a bonded state of the first circuit board to the second circuit board by solder, and the first reinforcing solder portions of the first circuit board and the second reinforcing solder portions of the second circuit board are arranged at positions facing each other when the second circuit board is laid on the first circuit board.

13. The image pickup apparatus for an endoscope according to claim 2,
further comprising first reinforcing solder portions provided in a periphery portion of the first circuit board and second reinforcing solder portions provided in a periphery portion of the second circuit board, for reinforcing a bonded state of the first circuit board to the second circuit board by solder, and
the first reinforcing solder portions of the first circuit board and the second reinforcing solder portions of the second circuit board are arranged at positions facing each other when the second circuit board is laid on the first circuit board.

* * * * *

UNITED STATES PATENT AND TRADEMARK OFFICE
CERTIFICATE OF CORRECTION

PATENT NO. : 10,039,437 B2
APPLICATION NO. : 15/493902
DATED : August 7, 2018
INVENTOR(S) : Fuminori Tanahashi Page 1 of 1

It is certified that error appears in the above-identified patent and that said Letters Patent is hereby corrected as shown below:

In the Claims

Column 16, Claim 1, Line 22 should read:
the part of each of the leads exposed in the Signed and Sealed this
Twelfth Day of February, 2019

Andrei Iancu
*Director of the United States Patent and Trademark Office*